United States Patent
Magelund et al.

(10) Patent No.: US 9,161,819 B2
(45) Date of Patent: Oct. 20, 2015

(54) ADJUSTABLE SUPPORT APPARATUS AND METHOD OF USING SAME

(71) Applicants: Alan Magelund, North Vancouver (CA); Alain Mercier, New Westminster (CA)

(72) Inventors: Alan Magelund, North Vancouver (CA); Alain Mercier, New Westminster (CA)

(73) Assignees: Alan Magelund, North Vancouver, British Columbia (CA); Alain Mercier, New Westminster, British Columbia (CA)

( * ) Notice: Subject to any disclaimer, the term of this patent is extended or adjusted under 35 U.S.C. 154(b) by 131 days.

(21) Appl. No.: 13/844,063

(22) Filed: Mar. 15, 2013

(65) Prior Publication Data

US 2014/0265496 A1  Sep. 18, 2014

(51) Int. Cl.
*F16M 11/00* (2006.01)
*A61B 19/00* (2006.01)

(52) U.S. Cl.
CPC ................................ *A61B 19/28* (2013.01)

(58) Field of Classification Search
CPC ....................................................... A61B 19/28
USPC ............ 248/181.1, 181.2; 297/314, 461, 338, 297/334.19; 482/121, 34
See application file for complete search history.

(56) References Cited

U.S. PATENT DOCUMENTS

| | | | |
|---|---|---|---|
| 2,719,571 A | 10/1955 | Taylor | |
| 3,754,787 A | 8/1973 | Garber | |
| 4,163,536 A | 8/1979 | Heller et al. | |
| 4,213,727 A * | 7/1980 | Lighthipe, Jr. | 414/420 |
| 4,650,249 A | 3/1987 | Serber | |
| 4,832,407 A | 5/1989 | Serber | |
| 5,022,708 A | 6/1991 | Nordella et al. | |
| 5,029,941 A | 7/1991 | Twisselmann | |
| 5,393,125 A | 2/1995 | Watson et al. | |
| 5,401,078 A | 3/1995 | Riach | |
| 5,762,402 A | 6/1998 | Gillotti | |
| 5,799,919 A | 9/1998 | Orr | |
| 5,921,628 A * | 7/1999 | Glockl | 297/338 |
| 5,971,485 A | 10/1999 | Clark | |
| 5,975,640 A | 11/1999 | Chen | |
| 6,224,154 B1 | 5/2001 | Stoki | |
| 6,397,414 B1 | 6/2002 | Lloyd | |
| 6,619,747 B2 | 9/2003 | Ko et al. | |
| 7,156,790 B2 * | 1/2007 | Johnsen | 482/146 |
| 7,337,483 B2 | 3/2008 | Boucher et al. | |
| 8,066,624 B1 * | 11/2011 | Stroup | 482/121 |

(Continued)

OTHER PUBLICATIONS www.ethos-surgical.com.

*Primary Examiner* — Amy Sterling
(74) *Attorney, Agent, or Firm* — Gowling Lafleur Henderson LLP

(57) ABSTRACT

An adjustable support apparatus used to support a person in a specific position over an extended period of time, and method of using the same. The apparatus has a base, an adjustable plate clamp assembly with upper and lower plates, a pivot within the apertures of the plates and adjustably retained between the plates, and a support member attached to the pivot and adapted to support a load. The adjustable plate clamp assembly has upper and lower plates. The upper plate has a central upper aperture, a first end pivotally attached to the base, and a second end. The lower plate has a central lower aperture, a first end, and a second end pivotally attached to the second end of the upper plate. The first end of the lower plate bears against the base, the plates together form an acute angle, and the apertures are aligned with one another.

9 Claims, 7 Drawing Sheets

(56) References Cited

U.S. PATENT DOCUMENTS

| | | | |
|---|---|---|---|
| 8,539,640 B1 * | 9/2013 | Waggener | 16/18 B |
| 8,540,314 B2 * | 9/2013 | Fernandez | 297/314 |
| 8,740,161 B2 * | 6/2014 | Hsu | 248/205.5 |
| 2004/0070253 A1 | 4/2004 | Murphy et al. | |
| 2010/0295357 A1 | 11/2010 | Koehler et al. | |
| 2011/0163577 A1 | 7/2011 | Anastasov | |

* cited by examiner

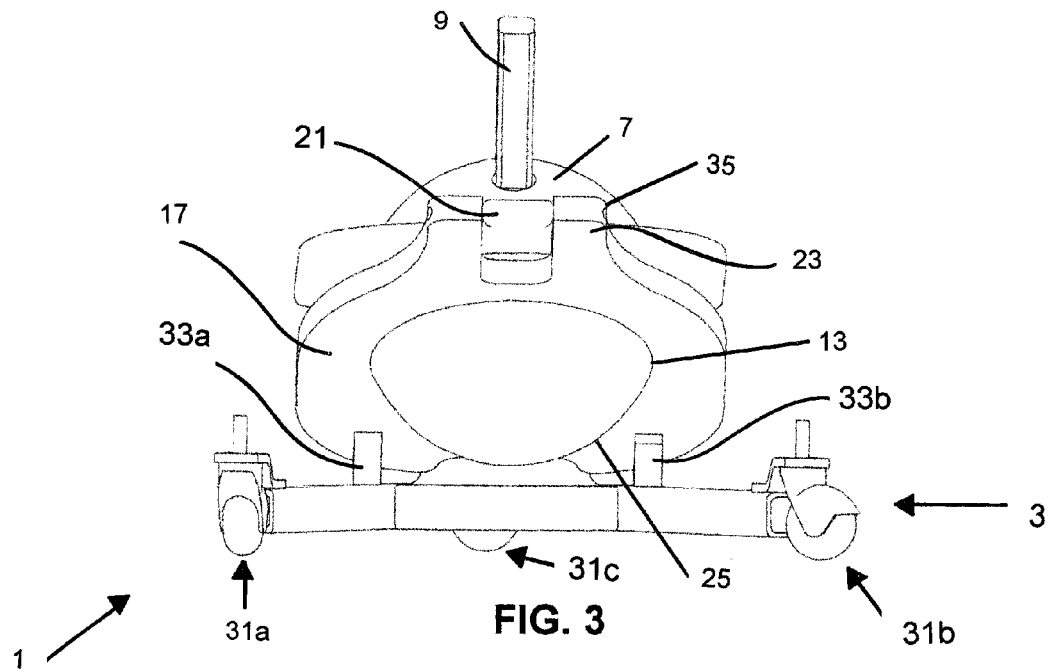
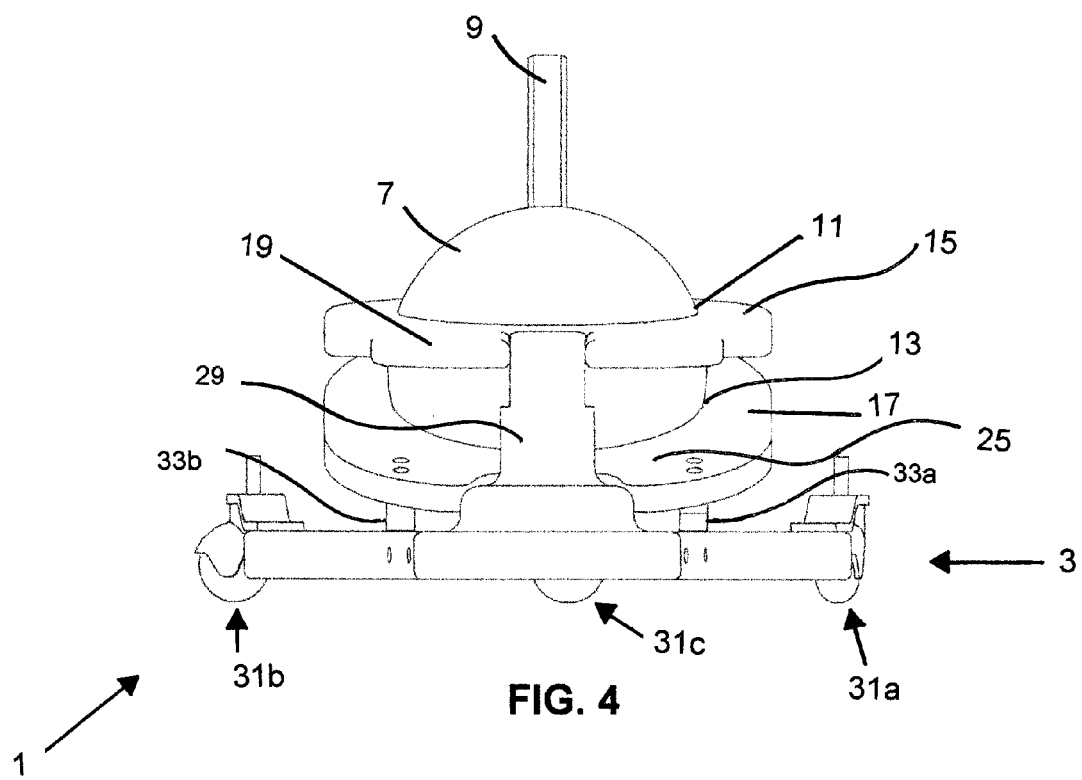

ADJUSTABLE SUPPORT APPARATUS AND METHOD OF USING SAME

1. TECHNICAL FIELD

The present invention generally relates to an adjustable support apparatus and method of using the adjustable support apparatus, and more particularly, to a hands-free adjustable support apparatus used for supporting a person performing a task while leaning over a work area. The present invention also generally relates to a method for efficiently adjusting the support apparatus between an unlocked and locked position in a hands-free manner using an external force.

2. BACKGROUND OF THE INVENTION

Surgeons, dentists and industrial workers often perform tasks that require sitting or standing in a fixed position for an extended period of time, such as when leaning over a patient for several hours during a surgical procedure. Surgical, dental, and operating room equipment and its arrangement may vary greatly depending on the particular surgical procedure and needs and preferences of a particular surgeon or dentist. For example, a surgeon or dentist may need to change his or her physical position throughout a surgical or dental procedure while avoiding contaminating his or her hands during such transition in order to prevent injury, such as back or neck strain, that may result from the surgeon or dentist sitting or standing in one position for an extended period of time. Thus, flexibility in adjusting the position operating room furniture and equipment is desirable. A hands-free, adjustable, ergonomic, support apparatus may help prevent such injury by supporting the surgeon or dentist's body and simultaneously avoid contaminating a sterile environment, such as an operating room.

The present invention is directed to an adjustable support apparatus for a person and a method of using the adjustable support apparatus that is adjustable in a hands-free manner for use in a sterile environment by a person who sits or stands in one position for an extended period of time.

3. SUMMARY OF THE INVENTION

One embodiment of the present invention is directed to a safe, stable, adjustable support apparatus and a hands-free method of using an adjustable support apparatus for ergonomically supporting a user, such as a surgeon, in a seated or standing position in order to mitigate or prevent lower back, neck, shoulder pain and body fatigue.

In one such embodiment, the apparatus of the present invention may be used to support a surgeon while the surgeon performs surgery on a patient in a sterile environment, such as an operating room, and adjusted in a hands-free manner.

In one such embodiment, the adjustable support apparatus comprises a base, a hinged clamp assembly fixed to the base, a pivot adjustably retained by the hinged clamp assembly, and a support member attached to the pivot and adapted to support a load, wherein the hinged clamp assembly comprises at least one aperture, the pivot is situated within the at least one aperture, and the hinged clamp assembly comprises a plurality of hinged clamp members.

More specifically, in one such embodiment, the adjustable support apparatus comprises a base, a hinged clamp assembly that is fixed to the base and comprises an aperture, a pivot located within the aperture and adjustably retained by the hinged clamp assembly, and a support member attached to the pivot which supports a load, for example, due to a person's weight, such as a surgeon's weight while using the apparatus with a seat while performing surgery on a patient.

More specifically, in one such embodiment, the adjustable support apparatus comprises a base, an adjustable plate clamp assembly with plates, a substantially curved pivot, including but not limited to a sphere-shaped pivot, situated within the apertures of the plates and adjustably retained between the plates, and a support member attached to the pivot and adapted to support a load. In an embodiment, the adjustable plate clamp assembly comprises upper and lower plates. The upper plate comprises a central upper aperture, a first end pivotally attached to the base, and a second end. The lower plate comprises a central lower aperture, a first end, and a second end pivotally attached to the second end of the upper plate. In an embodiment, the first end of the lower plate bears against the base, the plates together form an acute angle at the second ends of the plates, and the apertures in the plates are substantially coaxially aligned with one another.

In another embodiment, the method of using the apparatus of the present invention includes method of adjusting a support apparatus by providing a hands-free weight-activated adjustable support apparatus, unlocking or unloading the apparatus, for example, by exerting an upward force on the apparatus or by releasing an external force such the force due to a person's weight on the apparatus, and locking or loading the apparatus by exerting a downward force due to weight on the apparatus. More specifically, in one such embodiment, the method of using an adjustable support apparatus comprises the steps of providing the adjustable support apparatus, as discussed above, unloading or unlocking the apparatus by increasing the acute angle, for example, by exerting an upward force on the apparatus or by releasing an external force such the force due to a person's weight on the apparatus, changing the position of the pivot by moving the support member into a desired position, and loading or locking the apparatus by exerting a downward force on the apparatus and decreasing the acute angle.

Further advantages of the invention will become apparent when considering the drawings in conjunction with the detailed description.

4. BRIEF DESCRIPTION OF THE DRAWINGS

The adjustable support apparatus and method of using the apparatus according to the embodiments of the present invention will now be described with reference to the accompanying drawing figures, in which:

FIG. 3 illustrates a front view of the adjustable support apparatus shown in FIG. 1 for use in accordance with an embodiment of the present invention.

FIG. 4 illustrates a rear view of the adjustable support apparatus shown in FIG. 1 for use in accordance with an embodiment of the present invention.

Like reference numerals refer to corresponding parts throughout the several views of the drawings.

5. DETAILED DESCRIPTION OF THE INVENTION

The present invention is an adjustable support apparatus 1 and method of using the apparatus. The method employed may be used to adjust the position or angle of a device attached to it, such as a seat, support, platform, or the like, including, but not limited to, a surgeon's seat, in a hands-free manner by applying and releasing an external force, such as weight.

Figure 1:
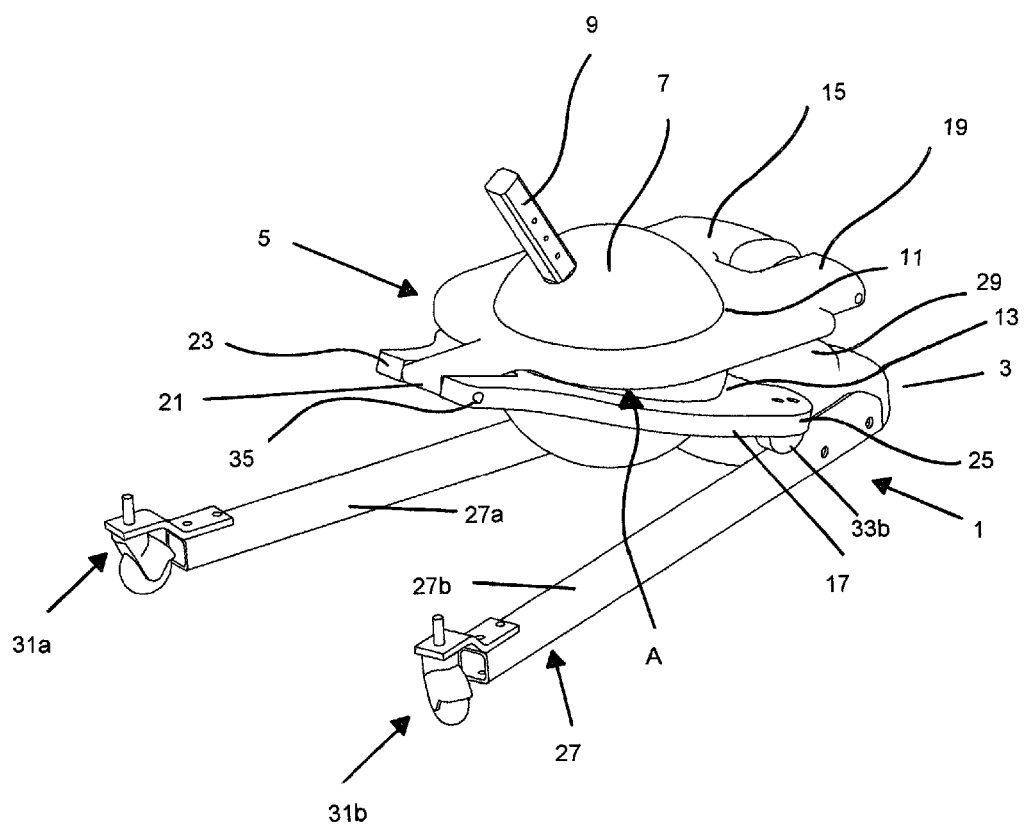
FIG. 1 illustrates a front perspective view of the adjustable support apparatus in accordance with an embodiment of the present invention.

FIG. 1 illustrates a front perspective view of the adjustable support apparatus 1 in accordance with an embodiment of the present invention. The adjustable support apparatus 1 may be used to support, for example, a surgeon's seat (not shown). The apparatus 1 comprises a base 3, an adjustable plate clamp assembly 5, a substantially spherical pivot 7, and a support member 9 attached to the pivot 7 and adapted to support a load, such as the weight of a person or object. The apparatus 1 may be stationary or moveable across a surface. In an embodiment, the base may be supported by wheels 31a, 31b, 31c (not shown) which permit the apparatus 1 to be moved horizontally across a surface by rolling. The wheels 31a, 31b, 31c (not shown) may be any type of wheels known in the art for supports, chairs, or vehicles used for supporting a person or heavy object, such as caster wheels. In an embodiment, the base frame may also have wheel locking mechanisms (not shown) for preventing rotation of the wheels. The wheel locking mechanisms may be any suitable wheel locking mechanism known in the art for supports, chairs, or vehicles used for supporting a person or heavy object, including but not limited to foot-activated brakes. In an embodiment, the wheels may have wheel frames (not shown) and wheel frame locking mechanisms (not shown) for preventing the wheels from swiveling.

The plate clamp assembly 5 comprises an upper plate 15 and a lower plate 17 that are pivotally connected to one another through, for example, a hinge or pin 35. The plates may be fabricated from any suitable materials, such as aluminum, stainless steel, iron, plastic, or other material with a suitable strength to weight ratio to support the weight of a person or heavy object. The upper plate comprises a central upper aperture 11 located in the center portion of the upper plate 15, a first end (or back) 19 that is pivotally attached to the base 3, and a second end (or front) 21. The lower plate also comprises a central lower aperture 13 located in the center portion of the lower plate 17, a first end (or back) 25, a second end (or front) 23 pivotally attached to the second end 21 of the upper plate 15. The first end 25 of the lower plate bears against the base 3. The lower plate 17 may also have a cam 33 affixed to the first end 25 of the lower plate 17, which bears against the base 3. In an embodiment, there are two cams 33a (not shown) and 33b, one affixed on each side of the lower plate 17. The upper and lower plates 15, 17 together form an acute angle A between them at the second ends 21, 23 of the upper and lower plates 15, 17. The upper and lower apertures 11, 13 in the plates are also substantially coaxially aligned with one another.

The pivot 7 is located within the apertures 11, 13 of the plates 15, 17 and adjustably retained between the upper and lower plates. The pivot may have a curved shape, including but not limited to a spherical, oblong, or cylindrical shape, and may be solid or hollow.

The base 3 may be formed as one uniform object or alternatively as a set of separate, discrete members connected to one another by any suitable connections or mechanical fasteners known in the art, such as welds or bolts, for example. In an embodiment, the base 3 comprises a horizontal base portion 27 with a plurality of outrigger arms 27a, 27b and a vertical base portion 29. In an embodiment, the outrigger arms 27a, 27b are configured in a "V" formation to enhance stability of the apparatus 1. The outrigger arms 27a, 27b each comprise a distal and proximal end portions. In an alternate embodiment (not shown), the horizontal base portion may comprise a plate.

Figure 2:
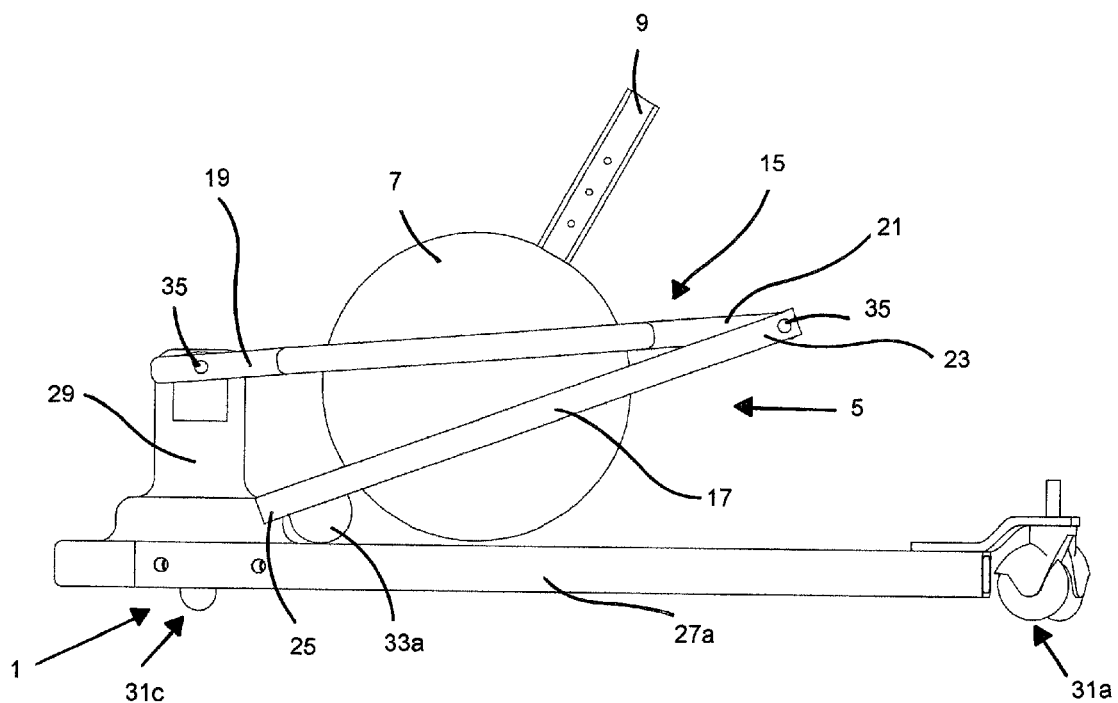
FIG. 2 illustrates a close-up side view of the adjustable support apparatus shown in FIG. 1 for use in accordance with an embodiment of the present invention.
Figure 5:
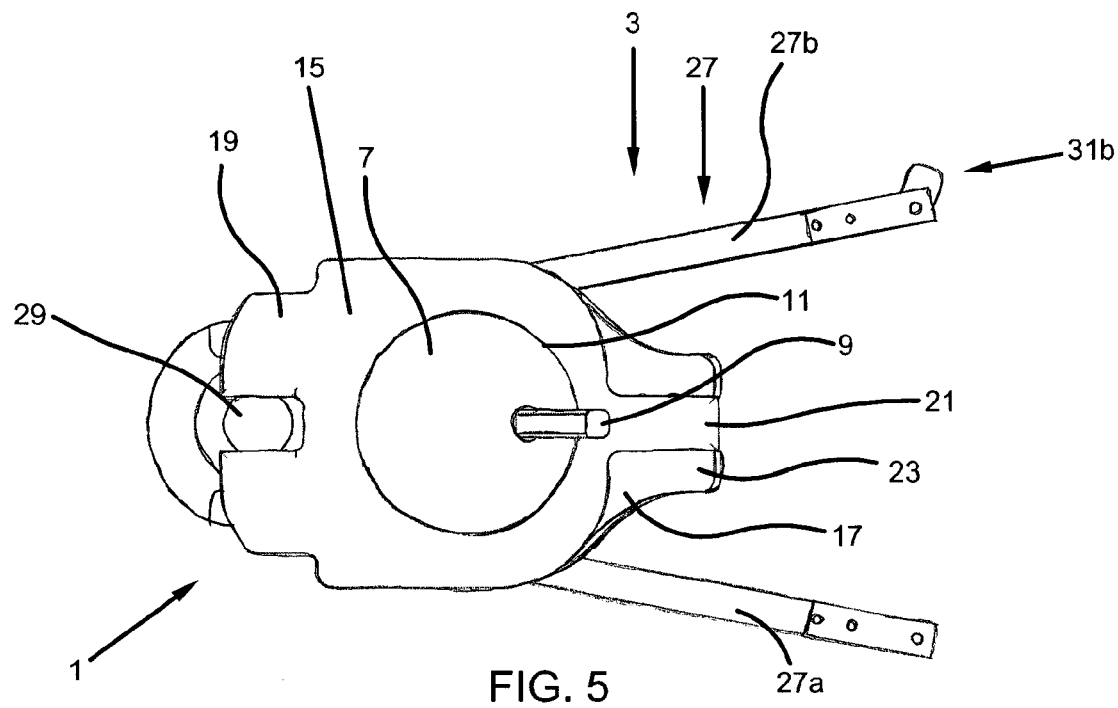
FIG. 5 illustrates a top view of the adjustable support apparatus shown in FIG. 1 for use in accordance with an embodiment of the present invention.
Figure 6:
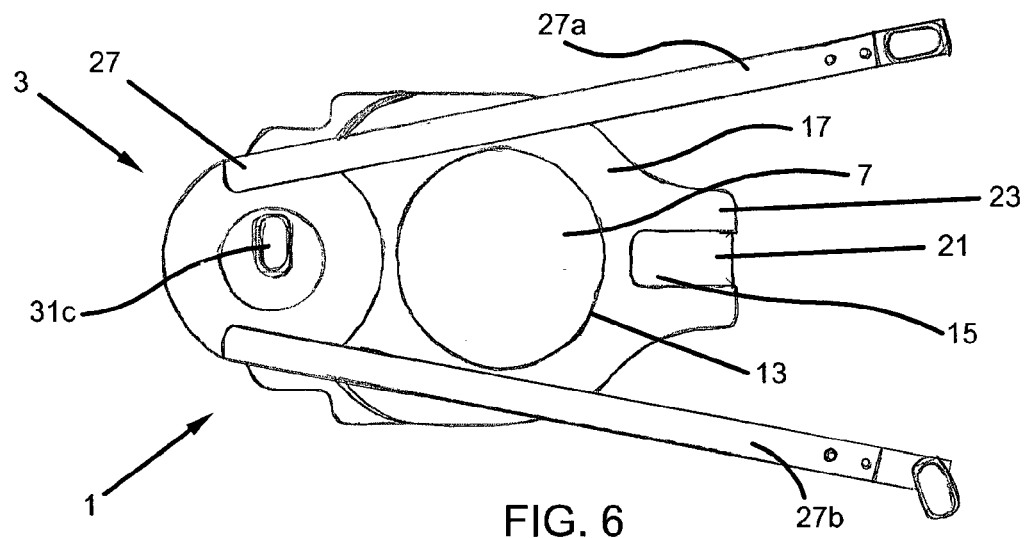
FIG. 6 illustrates a bottom view of the adjustable support apparatus shown in FIG. 1 for use in accordance with an embodiment of the present invention.

FIG. 2 illustrates a side view of the adjustable support apparatus shown in FIG. 1 for use in accordance with an embodiment of the present invention, where the apparatus is shown in a loaded position. FIG. 2 also illustrates a rear wheel 31c in the base 3 and shows cam 33a on first end 25 of lower plate 17.

FIGS. 3-6 illustrate front, rear, top, and bottom views respectively, of the adjustable support apparatus shown in FIG. 1, for use in accordance with an embodiment of the present invention where the base 3 comprises a rear wheel 31c. In an embodiment, cams 33a, 33b may be affixed to both sides of the first end 25 of the lower plate 17, for instance on a left and right side such that the cams 33a, 33b abut the outrigger arms 27a, 27b, thereby supporting the plate clamp assemblies.

Figure 7:
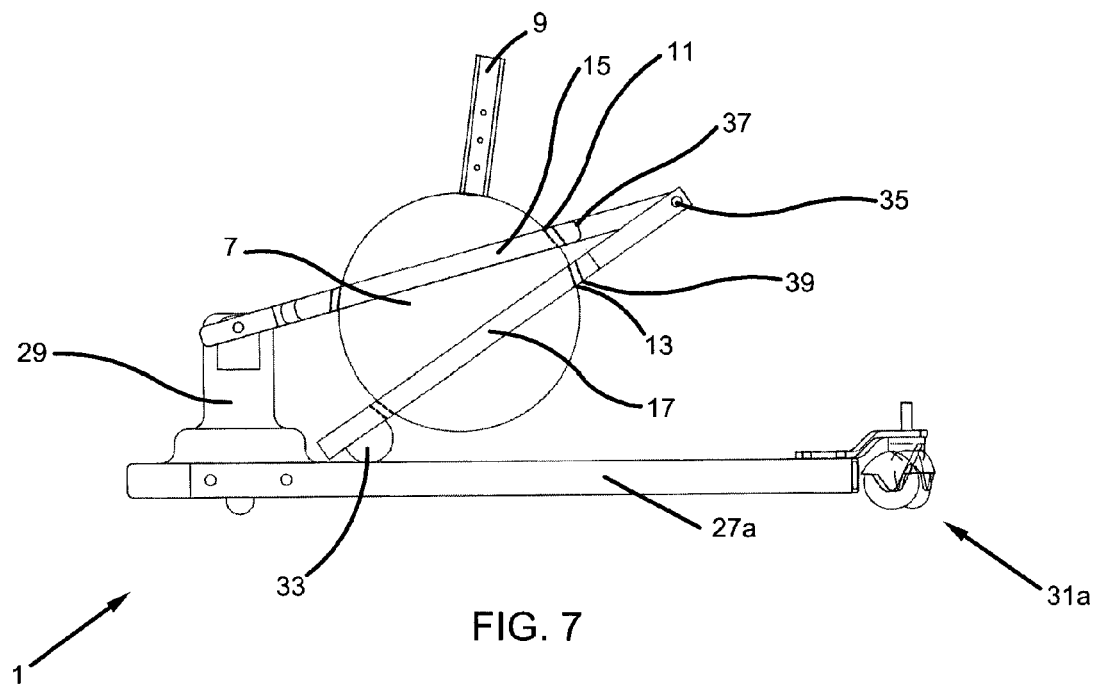
FIG. 7 illustrates a side view of the adjustable support apparatus shown in FIG. 1 in an unloaded position for use in accordance with an embodiment of the present invention.
Figure 8:
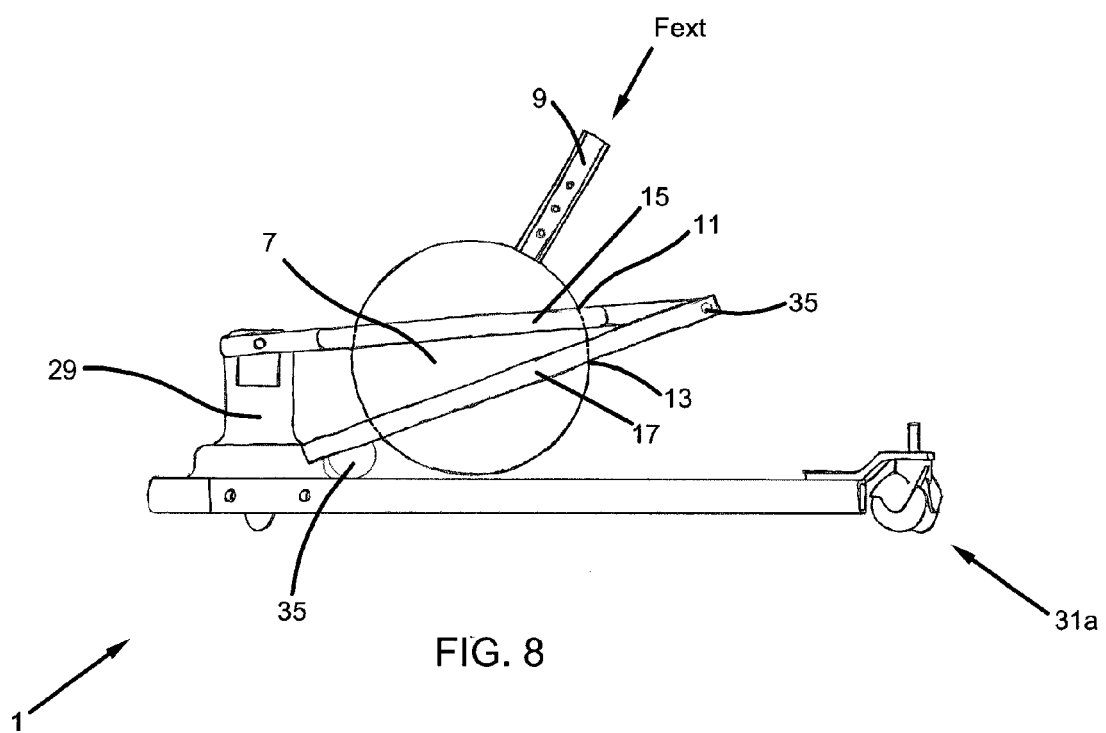
FIG. 8 illustrates a side view of the adjustable support apparatus shown in FIG. 1 in a loaded position for use in accordance with an embodiment of the present invention.

FIGS. 7-8 illustrate side views of the adjustable support apparatus shown in FIG. 1 in unloaded and loaded positions, respectively, for use in accordance with an embodiment of the present invention. FIG. 7 illustrates the apparatus 1 in an unloaded or unlocked position, where no external downward force is applied to the apparatus, such as a force due to weight imposed on the support member 9. In unloaded or unlocked position, the size of the apertures 11, 13 of the plates 15, 17 are greater than the respective cross sectional areas of the pivot 7 co-planar to the plates 15, 17 when it is situated within the apertures of the plates 15, 17, respectively, in this unloaded position. In an embodiment, the pivot 7 is spherically shaped. A spherically shaped pivot 7 is widest in its middle section and relatively narrow in its top and bottom portions. In other words, the cross sectional area of a sphere-shaped pivot 7 is greatest in its middlemost or equator section and decreases incrementally as one moves progressively away from the middlemost section, toward the top or bottom of the sphere 7. When the apparatus 1 is in an unloaded position, the upper plate 15 is situated above the widest, middle portion of the sphere, and the lower plate 17 is situated in below the widest, middle portion of the sphere. In this unloaded position, circular ring-shaped gaps 37, 39 are formed in the apertures 11, 13 between the spherically shaped pivot 7 and the respective plates 15, 17. These gaps permit the pivot 7 and support member 9 affixed to it to be moved manually or automatically freely through a wide range of motion, including but not limited to lateral and rotational movement, to the extent that the support member 9 may be rotated laterally until it abuts the side top surface of the upper plate 15 at the edge of the aperture 11.

FIG. 8 illustrates the apparatus 1 in a loaded or locked position, where an external force $F_{ext}$, such as the weight of a person or object, is applied to the apparatus, including but not limited to the weight due to a person sitting in a seat (not shown) that may be attached to the support member 9 of the apparatus 1. The support member 9 may be modular and removable from the pivot 7 or alternatively it may be permanently affixed or integrally formed with the pivot 7. In an embodiment, the external force may be actuated automatically using any suitable actuator known in the art, including but not limited to a motor. In the unloaded position, the size of the apertures 11, 13 of the plates 15, 17 in the apparatus 1 are substantially the same as the cross sectional areas of the pivot 7 when it is situated within the apertures of the plates 15, 17, respectively, in this loaded position. In an embodiment where the pivot 7 is spherically shaped, as discussed above, as the apparatus 1 is moved from an unloaded position, as illustrated in FIG. 7, to a loaded position as illustrated in FIG. 8, the upper plate 15 is moved from a position above the widest, middle portion of the spherical pivot 7, as discussed above, to a position that is closer to the wider, middle section of the spherical pivot 7, which decreases the size of the acute angle A between the plates 15, 17 and causes the ring shaped gaps 37, 39 to get progressively thinner, ultimately substantially disappear, allow the spherical pivot 7 and abut against the wall of the aperture 11, and form a substantially snug connection between the spherical pivot 7 and the upper plate 15. This snug connection between the pivot 7 and the plates 15, 17 prevents the pivot 7 and thus the support member 9 from being able to be moved when the apparatus 1 is in the loaded position. FIGS. 7 and 8 also illustrate how the sizes of the angle A between the plates 15, 17 and the ring-shaped gaps 37, 39 both decrease as the apparatus 1 is moved from an unloaded to a loaded position. As the external force $F_{ext}$ increases, the gaps 37, 39 decrease in size and virtually disappear to the naked eye, which restrains movement of the pivot 7 and support member 9 in the apertures 11, 13. Effectively the interior edge of the plates 15, 17, contiguously and circumferentially abut the pivot 7 in the locked or loaded position.

Figure 9:
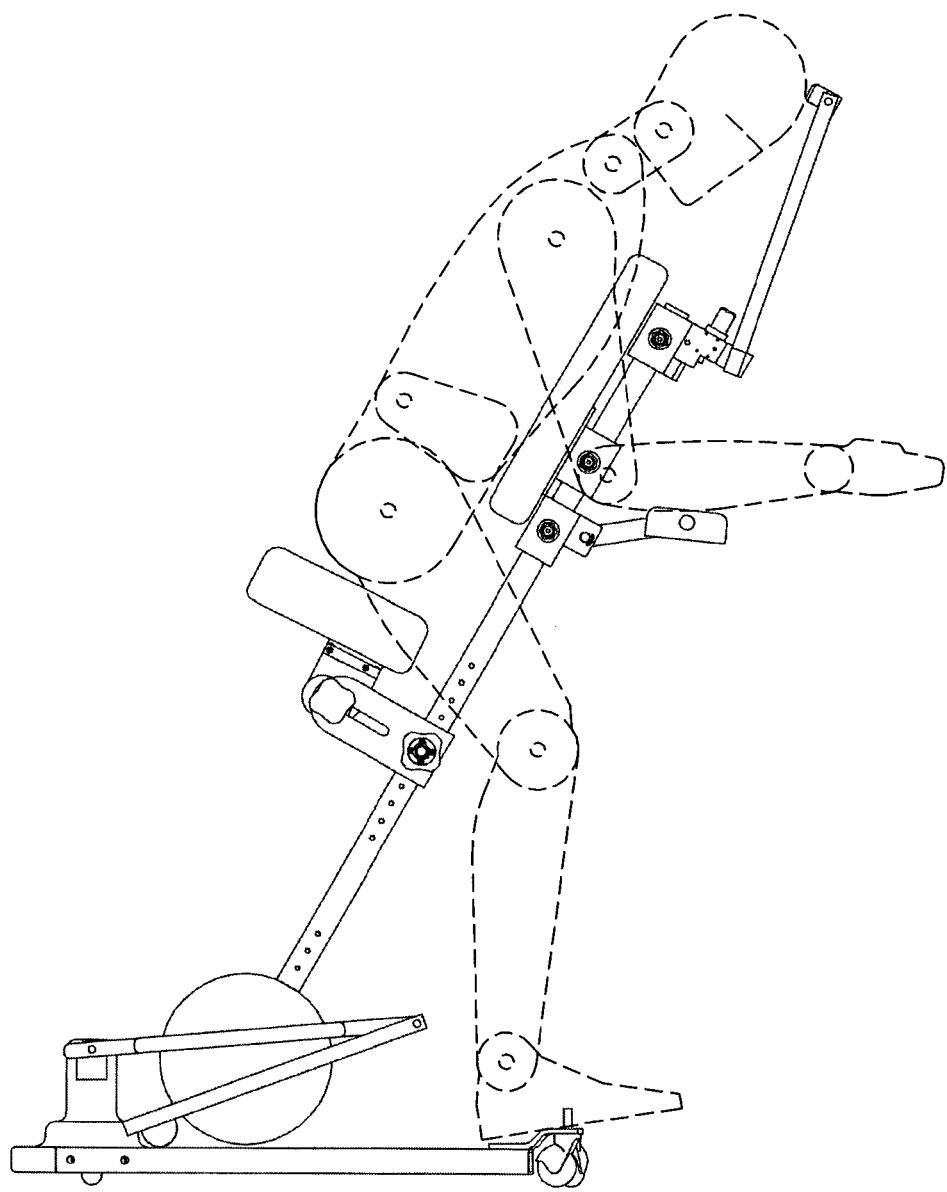
FIG. 9 illustrates a side view of the adjustable support apparatus shown in FIG. 1 in a loaded position and in use with a seat and other attachments in accordance with an embodiment of the present invention.

FIG. 9 illustrates a side view of the support apparatus 1 shown in FIG. 1 in a loaded position and in use with attachments 41, 42, 43, 44 in accordance with an embodiment of the present invention. The support apparatus 1 may be used to support objects, including but not limited to a seat 41, an arm rest 42, a chest support 43, a head rest 44, or a chin support (not shown). For example, in an embodiment, attachments, including but not limited to a seat 41, an arm rest 42, a chest support 43, a head rest 44, a chin support (not shown), or lighting assembly (not shown) may be attached to the support member 9 in order to provide more support to a surgeon who using the apparatus 1 while performing surgery on a patient, as illustrated in FIG. 9. The support member 9 may be fabricated from any suitable materials, such as aluminum, stainless steel, iron, plastic, or other material with a suitable strength to weight ratio to support the weight of a person or heavy object. The support member 9 may also be solid or hollow. In an embodiment, the support member 9 may be hollow in order to function as a conduit for cables, including but not limited to electrical cables used with a lighting assembly (not shown) or electric actuation and control system (not shown) for independently, automatically, and/or remotely controlling the apparatus's movement.

In an embodiment, the positions of the attachments 41, 42, 43, 44 may be permanently fixed in place or alternatively laterally, vertically, or rotationally adjustable with respect to the support member 9. The adjustment mechanisms may be any suitable adjustment mechanism known in the art, including but not limited to a friction knob or pin connection, as illustrated in FIG. 9. Alternatively, the positions of the attachments may be adjusted with respect to the apparatus 1 using a telescoping connection between the support member 9 and any member (not shown) to which the attachments are affixed.

Figure 10:
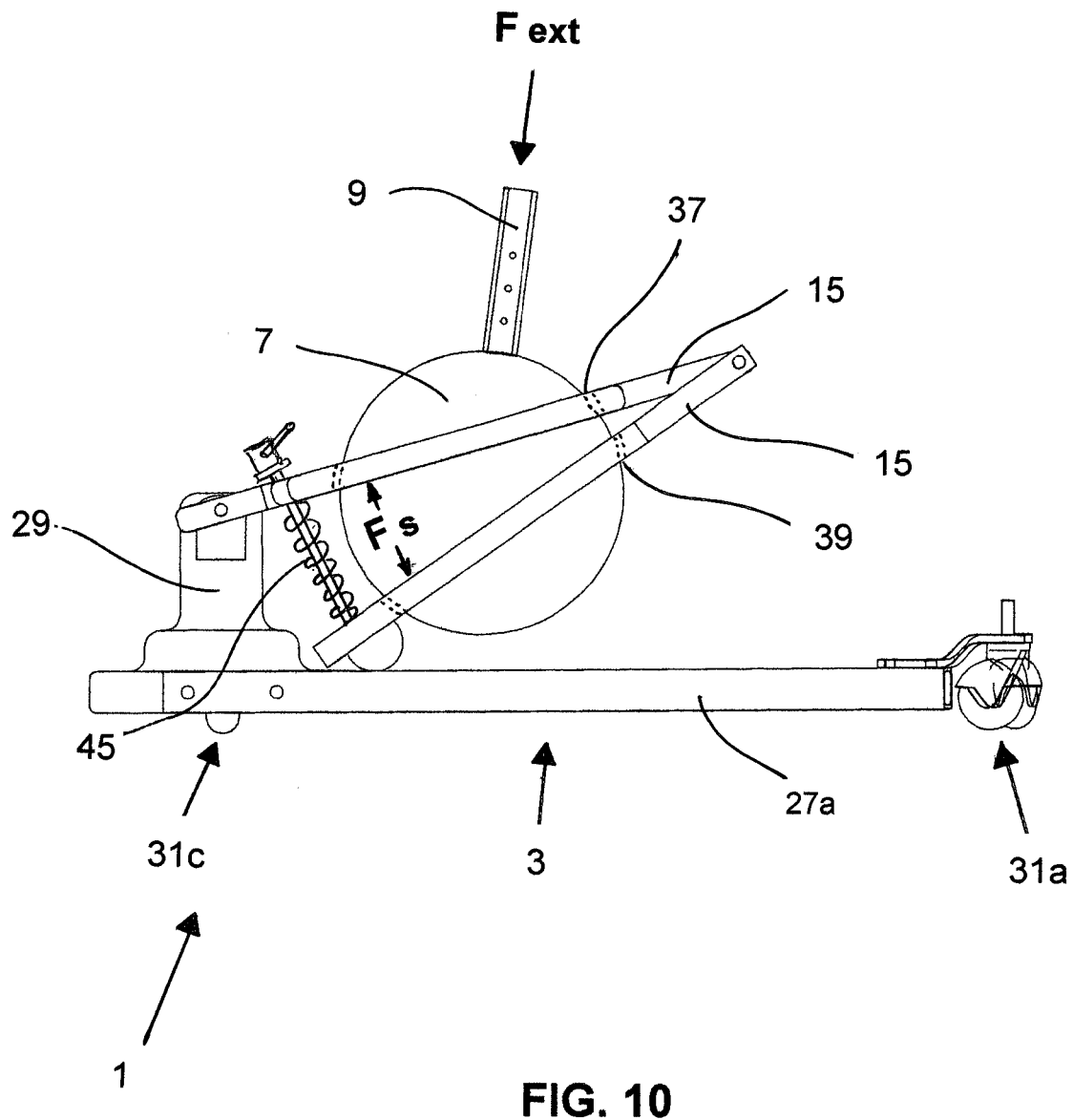
FIG. 10 illustrates a side view of an alternate embodiment of the adjustable support apparatus shown in FIG. 1 in a loaded position for use in accordance with an embodiment of the present invention.

FIG. 10 illustrates a side view of an alternate embodiment of the adjustable support apparatus 1 shown in FIG. 1 in a loaded or locked position for use in accordance with an embodiment of the present invention, where a resilient member, such as a spring 45, is situated between the plates 15, 17. A spring 45 may be used in the device to apply an upward force against the bottom side of the upper plate 15 and a downward force against the top side of the bottom plate 7 to maintain the apparatus 1 in an unloaded, unlocked position when the apparatus 1 is not in use. Any type of suitable device for exerting an upward force against the bottom side of the upper plate 15 and a downward force against the top side of the bottom plate 7 to maintain the apparatus 1 in an unloaded, unlocked position may be used, including but not limited to a coil spring 45, gas spring, bladder, pneumatic cylinder, compressible resilient material or the like. In an embodiment, the resilient member may be actuated and controlled automatically using any suitable hands-free actuator known in the art, including but not limited to an electric motor, foot actuated pedal, and electronic control system. The upward spring force imposed against the upper 15 plate counteracts any downward force on the upper plate 15 due to the weight of attachments, such as a seat, an arm rest, a chest support, a head rest, or a chin support, on the support member 9, in order to maintain the apparatus 1 in an unloaded position and prevent the weight of any attachments 41, 42, 43, 44 from pushing the apparatus 1 into a loaded or locked position. FIG. 10 illustrates the apparatus 1 with a spring 45 as an external force $F_{ext}$ is applied to the apparatus 1. FIG. 10 illustrates how the spring 45 interacts with the plates 15, 17 as the apparatus transitions from unloaded to a loaded position.

As discussed above, when the apparatus 1 is in an unloaded position where no external force is applied to the apparatus, such as a force due to weight imposed on the support member 9 by for example, attachments 41-44 or a person's weight, the upper plate 15 is situated above the widest, middle portion of a spherical pivot 7, and the lower plate 17 is situated in below the widest, middle portion of the spherical pivot 7, forming circular ring-shaped gaps 37, 39 in the apertures (not shown) between the pivot 7 and the respective plates 15, 17. These gaps 37, 39 permit the pivot 7 and support member 9 affixed to it to be rotated freely through a wide range of motion to the extent that the support member 9 may be rotated until it abuts the top surface of the upper plate 15. The force $F_s$ due to the spring 45 maintains the apparatus in this unloaded position in order to preserve these gaps 37, 39 regardless of whether is a minimal external force $F_{ext}$ is applied to the apparatus, such as the force due to the weight of attachments 41-44, that is substantially equal to or less than the spring force $F_s$. The spring 45 may be fabricated from any suitable materials, such as aluminum, stainless steel, iron, plastic, or other material with a suitable strength to weight ratio to support the weight of a person or heavy object. In an embodiment, the pivot 7 may be permanently locked into a desired position. In an embodiment, the apparatus 1 may also include a spring-loaded release lever.

The exemplary embodiments herein described are not intended to be exhaustive or to limit the scope of the invention to the precise forms disclosed. They are chosen and described to explain the principles of the invention and its application and practical use to allow others skilled in the art to comprehend its teachings.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims

What is claimed is:

1. An adjustable support apparatus comprising:
    a base,
    an adjustable plate clamp assembly comprising
        an upper plate comprising
            a central upper aperture,
            a first end pivotally attached to the base, and
            a second end,
        a lower plate comprising
            a central lower aperture,
            a first end,
            a second end pivotally attached to the second end of the upper plate, and
        wherein
            the first end of the lower plate bears against the base,
            the upper and lower plates form an acute angle at the second ends of the upper and lower plates, and
            the upper and lower apertures are substantially coaxially aligned with one another,
    a substantially curved pivot within the apertures of the upper and lower plates and adjustably retained between the upper and lower plates, and
    a support member attached to the pivot and adapted to support a load.

2. The adjustable support apparatus of claim 1, wherein the base comprises a horizontal base portion and a vertical base portion.

3. The adjustable support apparatus of claim 1, further comprising a cam affixed to the first end of the lower plate, the cam bearing against the base.

4. The adjustable support apparatus of claim 1, wherein
    the apparatus is in an unlocked position when upper and lower plates are disposed in positions along the pivot where the size of the apertures of the upper and lower plates are less than the cross sectional areas of the portions of the pivot disposed within the apertures, and
    the apparatus is in an locked position when upper and lower plates are disposed in positions along the pivot where the size of the apertures of the upper and lower plates are equal to the cross sectional areas of the portions of the pivot disposed within the apertures.

5. The adjustable support apparatus of claim 1, wherein the horizontal base comprises a plurality of outrigger arms, each of the plurality of outrigger arms comprising a distal end portion and a proximal end portion.

6. The adjustable support apparatus of claim 1, further comprising a wheel disposed on the horizontal base.

7. The adjustable support apparatus of claim 1, further comprising a spring disposed between the upper and lower plates.

8. The adjustable support apparatus of claim 1, further comprising a plurality of attachments affixed to the support member, the plurality of attachments selected from the group consisting of a seat, an arm rest, a chest support, a head rest, and a chin support.

9. The adjustable support apparatus of claim 1, further comprising a resilient member disposed between the upper plate and lower plate.

* * * * *